(12) United States Patent
Cropper et al.

(10) Patent No.: US 8,349,339 B2
(45) Date of Patent: Jan. 8, 2013

(54) ANTIPERSPIRANT OR DEODORANT COMPOSITIONS

(75) Inventors: Martin Peter Cropper, Wirral (GB); Kevin Ronald Franklin, Wirral (GB)

(73) Assignee: Conopco Inc., Englewood Cliffs, NJ (US)

( * ) Notice: Subject to any disclaimer, the term of this patent is extended or adjusted under 35 U.S.C. 154(b) by 1056 days.

(21) Appl. No.: 11/316,596

(22) Filed: Dec. 21, 2005

(65) Prior Publication Data

US 2006/0134037 A1 Jun. 22, 2006

(30) Foreign Application Priority Data

Dec. 22, 2004 (GB) .................................. 0428096.2

(51) Int. Cl.
*A61K 8/00* (2006.01)
*A61K 8/18* (2006.01)
*A61K 8/28* (2006.01)
*A61K 8/58* (2006.01)
*A61K 8/26* (2006.01)
*A61K 8/02* (2006.01)
*A61Q 15/00* (2006.01)

(52) U.S. Cl. ............... 424/401; 424/65; 424/66; 424/68

(58) Field of Classification Search .................... 424/65, 424/66, 68, 400, 401
See application file for complete search history.

(56) References Cited

U.S. PATENT DOCUMENTS

| | | | |
|---|---|---|---|
| 3,969,087 A | 7/1976 | Saito et al. ........................... 44/7 |
| 5,384,117 A | 1/1995 | Vu et al. ............................ 424/66 |
| 5,840,288 A | 11/1998 | Guskey et al. .................. 424/65 |
| 6,190,673 B1 | 2/2001 | Guskey et al. ................. 424/401 |
| 6,391,291 B1 | 5/2002 | Clare | |
| 6,410,003 B1 | 6/2002 | Bhatia et al. ..................... 424/65 |
| 6,652,843 B2 | 11/2003 | Fairclough et al. ............. 424/65 |
| 7,189,387 B2 * | 3/2007 | Chuah et al. ..................... 424/65 |
| 2002/0051757 A1 | 5/2002 | Clare et al. ..................... 424/65 |
| 2002/0159961 A1 | 10/2002 | Yamato et al. .................. 424/65 |
| 2003/0103920 A1 | 6/2003 | Cleare et al. ..................... 424/65 |
| 2003/0180239 A1 | 9/2003 | Bhatia et al. ..................... 424/65 |
| 2004/0186032 A1 | 9/2004 | Leone et al. .................. 510/147 |
| 2004/0213748 A1 | 10/2004 | Chuah | |
| 2004/0223995 A1 | 11/2004 | Emslie et al. ................. 424/401 |
| 2004/0223996 A1 | 11/2004 | Franklin et al. ................ 424/401 |
| 2004/0229984 A1 | 11/2004 | Yamato et al. ................ 524/198 |

FOREIGN PATENT DOCUMENTS

| | | |
|---|---|---|
| EP | 1 240 893 | 9/2002 |
| EP | 1 374 843 | 1/2004 |
| WO | 00/26285 | 5/2000 |
| WO | WO0158411 A2 | 8/2001 |
| WO | WO03005977 A2 | 1/2003 |
| WO | 03/059307 | 7/2003 |
| WO | 03/059308 | 7/2003 |
| WO | 2004/098552 | 11/2004 |

OTHER PUBLICATIONS

GB Search Report in a GB application GB 0428096.2.
PCT International Search Report in a PCT application PCT/EP 2005/012851.
X-Tend™ 226; International Specialty Products, Aug. 2003.

* cited by examiner

*Primary Examiner* — Mina Haghighatian
*Assistant Examiner* — Luke Karpinski
(74) *Attorney, Agent, or Firm* — Karen E. Klumas

(57) ABSTRACT

Segregation of antiperspirant actives suspended in anhydrous compositions employing ester oils or non-volatile silicone oils having a refractive index of at least 1.5, preferably together with an alcohol oil, gelled with a fibre-forming amide gellant can be inhibited by including a segregation inhibitor, especially an arylene-alkylene block copolymer, such as a tri-block copolymer e.g. a styrene/ethylenebutylene/styrene copolymer or a styrene/butylene copolymer.

47 Claims, No Drawings

ANTIPERSPIRANT OR DEODORANT COMPOSITIONS

FIELD OF THE INVENTION

The present invention relates to antiperspirant or deodorant compositions and in particular to compositions comprising a suspended particulate antiperspirant active and their preparation and use.

BACKGROUND OF THE INVENTION AND SUMMARY OF THE PRIOR ART

Antiperspirant compositions are widely employed throughout many parts of the world in order to control localised perspiration and thereby avoid wet patches which many societies consider to be unsightly, for example in axillary regions (the underarm) and less commonly to feet or other occluded body regions. Such compositions usually employ an astringent metal salt, such as most often an aluminium or aluminium/zirconium salt. Such salts are not only capable of blocking pores to inhibit and reduce sweating, but are also microbicidal and a significant fraction of the salts commonly remain on the skin surface between pores. By controlling perspiration with such salts, the user advantageously can simultaneously reduce or eliminate malodour generated locally. Accordingly, if insufficient antiperspirant active is present to enable the composition to function as an effective antiperspirant, the active normally provides deodorancy benefits.

Antiperspirant compositions containing effective concentrations of such astringent salts have been made or proposed in a range of different forms, for topical application, applied via non-contact applicators including liquid pump or squeeze sprays and aerosols, or via contact applicators including roll-ons for liquids, dispensers where a cream or gel is extruded through a narrow slit or aperture and sticks in which a solid is advanced though a wide aperture, often by an elevator coupled to a mechanism for advancing the elevator. A significant proportion of such compositions additionally comprise a carrier liquid for the antiperspirant active material. The liquid can be water-immiscible, in which case the antiperspirant can be present in particulate form suspended within the water-immiscible liquid. If desired, the carrier liquid can also be e thickened or solidified to form either a cream or a firm solid. Anhydrous creams are sometimes called soft solids, because unlike firm solids, they can be extruded under low force through narrow slits or apertures. In one class of products, of particular relevance to the present invention, the carrier fluid is structured or gelled to create a solid, which is commonly produced in the form of a stick, the stick usually, but not always, being housed within a dispensing container.

One aspect of consumer products to which consumers pay especial attention is the appearance of the product after application and likewise its sensory attributes. In addition, attention is often paid to the product before application. Many conventional antiperspirant products in stick or soft solid form that are distributed in the market place are opaque, white in appearance in the applicator pack and some of these are also white when applied onto the skin. Over the last 10 to 15 years, antiperspirant composition manufacturers have sought to offer alternative formulations, or at least publish such formulations in patent or other literature, which address one or other of the problems associated with avoiding white products, be they in the pack or after application onto the skin.

The principle has been disclosed by Vu et al in U.S. Pat. No. 5,384,117 of refractive index matching a suspended particulate antiperspirant active salt with a carrier liquid within about 0.02 units so as to achieve a relative turbidity of less than 800 FTU. In order to thicken or solidify the carrier liquid, he suggested employing a polymer as structurant (gellant) and employed in worked examples a polyethylene-vinyl acetate copolymer together with an aluminium chlorohydrate antiperspirant active. This structurant had a refractive index which was quite close to that of the other constituents. The choice of antiperspirant active exemplified, aluminium chlorohydrate, has a comparatively low refractive index, so that Vu did not provide suitable guidance as to how to achieve suitable clarity for compositions across his entire range and particularly for compositions containing an active with a higher refractive index, such an aluminium-zirconium actives. By comparison with Vu, it is desirable to employ alternative structurants that do not need to-be refractive index matched with the carrier liquid and suspended solid. If the polyethylene-vinyl acetate copolymer were used to solidify a composition employing a liquid carrier having a high refractive index that is suitable for aluminium zirconium actives, he would not achieve a translucent product, because there would be too great a disparity in refractive indexes of the carrier liquid and the structurant. Vu et al does not contemplate any problems arising from choice of a class of gellant that he does not mention or the effect of particle size distribution of the suspended particulate material and accordingly does not contemplate or even foreshadow the present invention.

Unilever has previously disclosed in WO 03/059308 that even if there is refractive index matching of the antiperspirant active particles and the gelled carrier liquid in which they are suspended, there can still be no guarantee of translucency. WO 03/059308 discloses that the particle size distribution of a suspended antiperspirant active can affect the clarity of a formulation in which it is suspended, the formulation advantageously comprising a carrier liquid of which at least 50% by weight comprises a non-volatile silicone oil and alkyl-aryl ester oil and which is solidified with a non-polymeric fibre-forming structurant. The text discloses that it is beneficial to select an antiperspirant solid of which less than 50% by weight of the particles have a diameter of up to 10 μm.

Further investigations into anhydrous antiperspirant sticks that compositions containing antiperspirant with a high proportion of comparatively large particles can suffer from other problems, including in particular segregation when a highly desirable class of gellants is employed.

One class of non-polymeric structurants which it is advantageous to employ to produce anhydrous antiperspirant sticks and particular anhydrous translucent sticks comprises fibre-forming amide gellants, but such gellants tend to have a high dissolution temperature in hydrophobic liquids that are employed in anhydrous antiperspirant formulations, and in particular in silicone oils and aryl-containing ester oils, the types of oils that enable a high refractive index carrier liquid to achieve translucency across a wide range of antiperspirant actives.

In the manufacture of anhydrous antiperspirant sticks a mixture of the gellant and the carrier liquid is fluidised by heating the mixture until the gellant melts/dissolves, the particulate antiperspirant active is mixed in, commonly after gellant dissolution, and the fluid mixture is thereafter filled into a mould or more usually directly into a dispensing container in which it cools to below its solidification temperature. The fluid mixture formulation is conventionally rendered homogenous in its processing vat or in distribution pipework by being mixed or otherwise subjected to shearing render, but once in the container the composition becomes quiescent because it is no longer practical to shear or mix the formulations. The instant inventors have found that the solidification temperature of anhydrous formulations gelled by fibre-forming amide gellants is sensitive to shearing, there being a significant drop in the solidification temperature from when compositions are being sheared to the same composition under quiescent conditions. Accordingly, since the temperature of the composition in the processing vat must be maintained above the shearing solidification temperature to avoid premature solidification, a larger temperature drop occurs in the container after filling to reach the quiescent solidification temperature. Comparatively large particles have a greater tendency to settle in quiescent liquid media than do smaller sized particles, so that a consequence of employing the larger sized antiperspirant particles (desirable to enhance translucency) with the combination of chosen carrier liquid and gellant is that there is a significant risk of segregation before the formulation solidifies or the viscosity of the suspending carrier fluid has increased to such an extent that particle settling is slowed sufficiently to prevent undue settling.

The employment of N-acyl aminoacid amide gellants to solidify oil compositions has been disclosed previously in U.S. Pat. No. 3,969,087 and specifically antiperspirant compositions in US 2002/0159961, US 2004/0229984, WO 2004/098552 and WO 2004/098553. Antiperspirant compositions in which an oil phase is solidified with selected dipeptide gellants are described in WO 03/059306 and WO 03/059307. Antiperspirant compositions in which an oil phase is solidified with selected bis amido gellants and particularly gellant derive from 1,2 or 1,3 bis amidocyclohexane are described in U.S. Pat. No. 6,410,003. Formulations in which amide derivatives of di and tribasic carboxylic acids gel an oil phase are described in U.S. Pat. No. 5,840,288 and U.S. Pat. No. 6,190,673B1. None of these specifications contemplate particle segregation when employing comparatively large antiperspirant particles, nor any means to ameliorate or overcome segregation.

Accordingly, it is an object of the present invention to identify means to ameliorate or overcome settling of a particulate antiperspirant in a carrier liquid comprising a silicone and/or aryl-containing ester oil that is gelled with a fibre-forming amide gellant.

STATEMENT OF THE INVENTION

According to a first aspect of the present invention, there is provided a composition in accordance with claim 1 hereinafter.

According to a second aspect of the present invention there is provided a process for preparing an antiperspirant composition in accordance with claim 44.

According to a third aspect of the present invention there is provided a method of reducing sedimentation in an antiperspirant composition in accordance with the method according to claim 46.

Herein by the term fibre-forming amide gellant is meant a monomeric or dimeric gellant containing at least one amide linkage, having a molecular weight below 1,500 which gels a water-immiscible oil (of which 50/50 w/w mixture of D5 [pentacyclodimethicone] and isostearyl alcohol is a representative oil) at a concentration within the range of 1 to 15% by weight forming a network of thin primary strands or fibres extending throughout the gelled oil. Thin indicates that the primary strands or fibres cannot be detected by the unaided human eye, usually having a diameter when viewed in an electron microscope of not greater than 0.5 μm and in many cases not greater than 0.2 μm. The primary strands or fibres appear to have numerous branches or interconnections and may link together or entwine to form a thicker strand.

A non-volatile silicone oil has a vapour pressure of less than 1 Pa at 25° C.

By virtue of the selection of a fibre-forming amide gellant, it is often possible to obtain an anhydrous antiperspirant stick with only a low concentration of gellant for the specified carrier liquid, but as indicated hereinabove, such formulations can suffer from particle segregation. By virtue of the dissolution of a segregation inhibitor, as typified by an arylene/alkylene block copolymer, into a fluid composition comprising the carrier fluid, particulate antiperspirant active and dissolved fibre-forming amide gellant before the composition is filled into a dispensing container or a mould, the inhibitor retards the rate of settling of the particles of antiperspirant salt whilst the composition is in the container or mould and cooling to below its quiescent solidification temperature, it being impractical to employ external mixing or shearing within the container or mould. As a consequence of retardation of settling, the extent of preferential settling of larger particles is diminished and in consequence, segregation is diminished. This is beneficial in that the efficacy of the antiperspirant product does not vary so much during the use-up of the product. The relative proportions of inhibitor and gellant are of crucial importance, a ratio of at least 1:1 being needed.

As a second benefit, the addition of the segregation inhibitor, particularly the block copolymer as indicated above, enables the formulator to take advantage of translucency of formulations obtainable using an antiperspirant active salt, preferably having only a small or reduced fraction of particles having a particle diameter of below 10 μm, together with a fibre-forming amide gellant and reduce the segregation of antiperspirant active salt that would otherwise occur. In other words, the formulator can combine the ability to achieve translucency with reduced particle segregation whilst employing a selected gellant.

DETAILED DESCRIPTION OF THE INVENTION INCLUDING PREFERRED EMBODIMENTS THEREOF

The present invention relates to antiperspirant compositions, a process for their preparation and a means for ameliorating segregation of the suspended particulate active employing a desired class of gellant for the specified carrier liquid.

Herein, the gellant comprises at least one fibre-forming amide gellant. Such gellants are preferably chosen from N-acyl aminoacid amides, cyclic dipeptides, 1,2 or 1,3 bisamidocyclohexanes and amide derivatives of 1,2 or 1,3 di or 1,2,3 tri carboxylic acids, which are sometimes referred to hereinafter as gellants (1), (2), (3) or (4). respectively.

N-acyl aminoacid amides are preferably selected from general formula (1a) [gellant (1a)] and/or (1b) [gellant (1b)] disclosed hereinafter and especially desirably comprises at least one gellant that satisfies formula (1a). An N-acyl aminoacid amide that satisfies general formula (1a) is sometimes referred to herein as gellant (1a). General formula (1a) has the formula $A^X$-CO—$R^X$ in which $A^X$ represents the residue of an amino acid amide and $R^X$ represents a branched alkyl group containing from 4 to 12 carbon atoms and sometimes 7 to 10 carbon atoms. In many instances, the aminoacid amide residue $A^X$ can be represented by general formula (2)

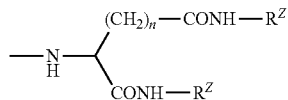

in which n represents an integer of 1 or 2 and $R^Z$ represents an alkyl group, which can be linear or branched, containing from 1 to 10 and particularly from 3 to 5 carbon atoms, each of which $R^Z$ groups can be the same or different. Accordingly, the amino acid from which such an amide residue $A^X$ is derivable is glutamic or aspartic acid. In some especially preferred embodiments, each $R^Z$ represents a butyl group, especially an n-butyl group, and particularly in the derivative of glutamic acid, which residue is represented by formula (3)

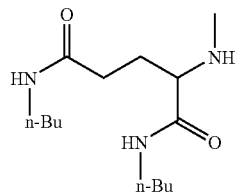

In formula (1), $R^X$ preferably represents an alkyl group containing either one or two or possibly three side chains, such as particularly one side chain. Desirably, any side chain in $R^X$ contains from 1 to 4 carbon atoms, such as methyl, ethyl propyl or butyl, and often from 1 to 3 carbon atoms, of which ethyl is very convenient. The alkyl backbone preferably contains from 4 to 8 carbon atoms and often from 4 to 7 carbon atoms, or particularly 7 or 8 carbon atoms. The location of the side chain along the alkyl group backbone is at the discretion of the producer, of which the 2 position is often favoured. An especially desirable branched chain group for $R^X$ is 1-ethylpentyl, so that the resultant acyl group is 2-ethylhexanoyl. Other branched chain groups for $R^X$ include 1-methylbutyl, isobutyl and 1-butylheptyl. It is particularly desirable to employ a gellant (1a) in which $R^X$ is according to one or more of the branched alkyl groups named above and the amide residue is derived from glutamic acid dibutylamide. A convenient and highly desirable example of a gellant (1a) is available from Ajinomoto as GA-01™.

Although it is preferable to employ at least one N-acyl aminoacid amide in accordance with formula (1a) alone, it is preferable to employ it together with another N-acyl aminoacid amide such as those which satisfy general formula (1b), sometimes referred to herein as gellant (1b).

In some embodiments, gellant (1a) is desirably employed in conjunction with a second amide-fibre-forming structurant, gellant (1b). N-acyl aminoacid amides according to gellant (1b) are described in U.S. Pat. No. 3,969,087. A list of many of such named amides and the general method of manufacture of them is described in said patent specification in column 1 line 63 to column 4 line 47, and specific amido derivatives are named in Example 1 in column 6 to 8, which passages from the text are incorporated herein by reference. Herein, gellant (1b) satisfies formula (1b) $A^y$-CO—$R^Y$ in which $A^Y$ represents an amino acid amide residue and $R^Y$ represents a linear alkyl group containing from 9 to 21 carbon atoms. Highly desirably, $A^Y$ represents an amino acid amide in accordance with the formula (5)

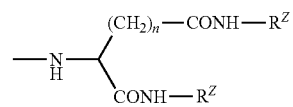

in which n represents an integer of 1 or 2 and $R^Z$ represents an alkyl group, which can be linear or branched, containing from 1 to 10 and particularly from 3 to 5 carbon atoms, each of which $R^Z$ groups can be the same or different. Accordingly, the amino acid from which such an amide residue $A^Y$ is derivable is glutamic or aspartic acid. In some especially preferred embodiments, each $R^Z$ represents a butyl group, especially an n-butyl group, and particularly is the derivative of glutamic acid. This is likewise represented by formula (3) given supra for residue $A^X$.

In formula (1b), $R^Y$ often contains from 9 to 15 linear carbons, of which one preferred group comprises undecyl. N-Lauroyl-L-glutamic acid di-n-butylamide, formula (6)

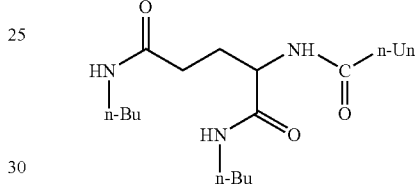

(n-Un=undecyl) employed in Example 14 of '087, is an especially desirable amide structurant for employment in the instant invention compositions and is commercially available from Ajinomoto under their trade designation GP-1.

The second class of amide gellants (2) suitable for employment in the instant invention comprises structurants which satisfy the following general formula (7):

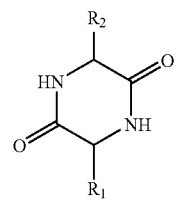

in which one of $R_1$ and $R_2$ represents an alkyl, alkyl ester group and the other represents an alkyl or alkaryl group. Examples of such amides are described in two papers by Hanabusa et al, entitled respectively Cyclo(dipeptide)s as low molecular-mass Gelling Agents to harden Organic Fluids, J. Chem Soc. Commun., 1994 pp 1401/2, and Low Molecular Weight Gelators for Organic Fluids: Gelation using a Family of Cyclo(dipeptide)s, in the Journal of Colloid and Interface Science 224, 231-244 (2000), which descriptions of amide structurants are incorporated herein by reference.

However, it is especially preferred to employ herein a subclass of cyclodipeptides not expressly disclosed by Hanabusa, which sub-class satisfies the general formula (8):

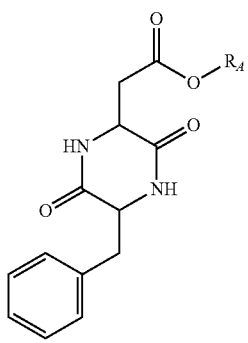

in which $R_A$ represents a carbocyclic or heterocyclic group containing not more than 2 rings. Such materials are sometimes herein referred to as DOPA derivatives.

In DOPA derivatives, $R_A$ can comprise two fused rings, but preferably comprises a single six membered ring, either carbocyclic or heterocyclic, or a bridged ring. When A is carbocylic, it can be either saturated or unsaturated, preferably unsaturated or aromatic. When $R_A$ is heterocyclic, it is preferably saturated.

Although the cyclic group within $R_A$ can be unsubstituted, it is preferably substituted by at least one alkyl substituent, which preferably contains no more that 16 carbon atoms. In some highly desirable embodiments the alkyl substituent has a longest chain length of up to 4 carbon atoms, and in certain or those a total carbon content of up to 5 carbon atoms. The alkyl substituent may be linear or branched.

Preferred examples include methyl, ethyl, propyl, isopropyl, butyl isobutyl or t-butyl or isopentyl. In a number of very suitable DOPA derivatives, $R_A$ contains two or more alkyl substituents and especially those selected from the above list of preferred examples. The alkyl substituents may be the same, such as two or more methyl substituents, or may be a combination of different substituents such as a methyl and isopropyl substituents. When $R_A$ is saturated, the substituents may depend from the same carbon atom in the ring, such as two methyl groups, or from different carbon atoms. In several highly desirable derivatives, two alkyl substituents are meta or para-to each other, for example meta methyl groups or a para methyl and isopropyl group. In yet other derivatives, the ring may include a methylene bridge, which preferably likewise completes a six membered ring.

In some suitable DOPA derivatives, the or one alkyl substituent may be ortho or para to the bond with the DOPA residue, as in 4-methyl-phenyl-. In some or other DOPA derivatives, the bond with the DOPA residue is meta to one or preferably two methyl substituents.

When $R_A$ is heterocyclic, the heterocyclic atom is suitably nitrogen. Conveniently, the heterocyclic atom can be para to the bond with the DOPA residue. Moreover, in a number of desirable derivatives, the heteroatom is ortho to at least one alkyl group, better in a saturated ring and especially to up to 4 ortho methyl groups.

The group $R_A$ is often most easily referred to as the residue from the corresponding alcohol which may be reacted with DOPA to form the ester linkage. Thus, desirable examples of $R_A$ include the residues from 4-alkyl phenol, such as 4-nonylphenol, and 2,6-dialkyl- or 2,2,6,6-tetraalkyl-4-piperidinol, such as 2,2,6,6-tetramethyl-4-piperidinol.

In some preferred DOPA derivatives, the ring in $R_A$ is carbocyclic, and is substituted by at least two alkyl groups of which at least one is methyl and the other or one of the others is isopropyl. Examples of such preferred $R_A$ residues include menthol, isopinocamphenol and 3,5-dialkyl cyclohexanol such as 3,5-dimethyl cyclohexanol. Especially preferred $R_A$ residues include thymol. Yet others include the DOPA derivatives from carveol and carvacrol.

The DOPA derivatives used in this invention may be a mixture of compounds within the general formulae given, or may be a single compound.

The DOPA derivatives can be prepared by reacting the respective alcohol with DOPA in acid form (DOPAA), or possibly with an acid chloride, or possibly an anhydride or an ester containing a DOPA residue. DOPAA can be obtained by cyclising aspartame. DOPAA can be reacted with the relevant alcohol of formula $R_A OH$, preferably in a mole ratio to the DOPAA of at least 2:1 in dimethyl sulphoxide, in a ratio of from 6:1 to 12:1, in the presence of a promoter, such as a carbonyldiimidazole, in an amount preferably from 0.5 to 2 moles of promoter per mole of DOPA acid. The reaction is conveniently carried out at a temperature from 40 to 60° C.

Such fibre-forming amide gellants (2) and their preparation are detailed in WO 03/059307, the passages therein that are relevant to respectively the compounds or their preparation being incorporated herein by reference.

The third class of amide fibre-forming gellants, (3) comprises di-amido and triamido-substituted cyclohexane. Particular sub-classes of such compounds comprise -1,2 or -1,3 substituted cyclohexane compounds, and 1,3,5-triamido-substituted cyclohexane in which the amido group desirably accords with the general formula $—(CH_2)_v—CO—NH—R^{111}$ and $—(CH_2)_v—NH—CO—R^{111}$) in which $R^{111}$ represents an alkyl group of from 5 to 27 carbon atoms and v is an integer selected from zero and one.

When the cyclohexane ring is substituted by two amido substituents, the substituents preferably satisfy $—(CH_2)_v—NH—CO—R^{111}$) and are very desirably in the 1,2 or 1,3 positions relative to each other around the cyclohexane nucleus. When they are in the 1,3 relative positions, v preferably represents 1. When the two substituents are in the 1,2 relative position, v preferably is zero.

When the cyclohexane ring is substituted by three amido groups, they each preferably satisfy $—(CH_2)_v—CO—NH—R^{111}$.

$R^{111}$ can be linear or branched. Preferably the number of carbons in $R^{111}$ is selected in the range of 8 to 20. For example undecyl, dodecyl, 2-ethylhexyl, octadecyl, or dimethyloctyl.

Such fibre-forming amide gellants (3) and their preparation are detailed in U.S. Pat. No. 6,410,003, the passages therein that are relevant to respectively the compounds or their preparation being incorporated herein by reference.

A fourth sub-class of amide structurants suitable for employment herein, gellant (4) comprises amide derivatives of 1,2 or 1,3 di and 1,2,3 tribasic carboxylic acids, that is to say carboxylic amide derivatives from adjacent aliphatic carbons or aliphatic carbons separated by a single carbon. Such gellants are in accordance with the description either as set forth in U.S. Pat. No. 5,840,288 and specifically the passage from column 12. line 37 to column 14 line 20 or as set forth in U.S. Pat. No. 6,190,673B1, specifically the passages col 1 line 47 to col 2 line 38 and col 3 line 47 to col 5 line 23. Their general methods of manufacture are as described in the passage in U.S. Pat. No. 5,840,288 in column 12 line 37 to 39 or as set forth in U.S. Pat. No. 6,190,673B1, in the passage in col 5 lines 28 to 43. Specific suitable gellants (4) are listed in column 13 line 62 to column 14 line 7 in U.S. Pat. No. 5,840,288 and in Table 1 in col 13 of U.S. Pat. No. 6,190,673B1. Convenient carboxylic acid for the preparation of amide derivatives include succinic acid and aliphatic acids containing three vicinal carboxylic acid groups such as 1-propene-trioic acid. Each amide substituent preferably contains an alkyl, especially linear alkyl group of from 3 to 12 carbons. A particularly preferred gellant (4) is 2-dodecyl-N,N'-dibutylsuccinamide or 1-propene-1,2,3-trioctylamide or 2-hydroxy-1,2,3-propane-tributylamide. Such passages are incorporated herein by reference. In a further variation, the triamido gellants can satisfy the general formula $CH[(CH_2)_xCONR^yR^z]_3$ in which each x, $R^y$ and $R^z$ may be the same or different, x being from 0 to 3, $R^y$ being a hydrocarbon containing 1 to 3 carbons and $R^z$ being a hydrocarbon containing from 6 to 24 carbons. Such tri-amido gellants are described in WO 2005/082839.

The weight proportion of the fibre-forming amide gellants and particularly gellants (1) to (4) in the composition is commonly selected in the range of 0.6 to 10%, taking into account the inherent gelation capability of the gellants. The range of 0.5 to 2% gellant is particularly suitable for gellant (2). At least 2% of gellant (1), (3) or (4) is preferably employed, particularly at least at least 2.5% w/w and especially at least 3% w/w. It many compositions, the weight proportion of the fibre-forming amide gellant is up to 8% and in a number of preferred compositions is up to 6% w/w in the composition. The gellant can be selected from a single class of gellant or can comprise a mixture of gellants from two or more classes.

The proportion of amide gellants such as gellant (1) to gellant (4) in the composition can also be stated in relation to the water-immiscible phase (carrier liquid or mixture of carrier liquids) which it is structuring (gelling). The weight proportion of such gellants is usually selected in the range of from 1 to 15% w/w of the carrier liquid, and is often present in a proportion of at least 2% w/w of that phase. When a gellant (1), (3) and/or (4) is employed, it is highly desirable for it to constitute at least 3% by weight of the carrier liquid. Its weight proportion of that carrier liquid in a number of preferred embodiments is up to 12%. In some desirable embodiments, the weight proportion of the amide gellant(s) in the carrier liquid is at least 6%. In some convenient embodiments, the weight proportion of amide gellant(s) in the carrier liquid is up to 10%.

It is especially desirable to employ gellant (1) or a combination of gellants within gellant (1) as the amide gellant or as at least half of a mixture with one or more other class of gellants, such as gellant (2) or (3). However, if desired, stick producers can employ any mixture of gellants (1), (2), (3) and (4) that they wish, provided that the total weight proportions of fibre-forming amide gellant are in accord with the foregoing disclosures.

It is especially desirable to employ a mixture of at least one from each of (1a) and (1b). The weight ratio of gellant (1a) to gellant (1b) is often selected in the range of from 4.5:1 to 1:0, suitably from 4.5:1 to 1:4.5 and commonly from 3:1 to 1:3. In many instance the weight ratio is no higher than 2:1 and in such or other instances, the weight ratio is at least 1:2. A convenient weight ratio can be in the range of 1.1:1 to 1:1.1.

It is preferable to employ sufficient gellant or mixture of gellants for the resultant composition at ambient temperature (22° C.) to be a stick (a solid, not a semi-solid) which in a standard penetrometer test is penetrated $\geq$20 mm. In the standard test, conducted at 22° C., a clean needle (2.5 g, Seta Wax Penetration needle™ having a tip angle of 9° 10'+/−15") mounted in a plunger (47.5 g) with its tip 0.5 mm above and then lowered gently onto the freshly cut surface of the sample to be tested, when the tip just touches its shadow. The apparatus then permits the plunger and needle to drop for 5 seconds penetration, and the depth measured immediately (i.e. no delay). The procedure is repeated 5 times to obtain an average.

Segregation Inhibitor

The instant invention employs a material that retards the rate at which a particulate material, the antiperspirant active, settles in a quiescent hydrophobic carrier liquid at an elevated temperature, and especially in the temperature range between the solidification temperature of the composition under sheared conditions compared with quiescent conditions. It is during cooling between those two temperatures plus the additional temperature difference between the shearing solidification temperature and the fill temperature that particle settling and hence segregation occurs. It will be understood in conventional filling processes, usually into a dispensing container, but sometimes into a mould, the composition is still fluid when the filling takes place, commonly having been cooled to a temperature of from 3 to 10° C. above the shearing solidification temperature, e.g. 5 or 6° C. above. Whilst the composition remains in a processing vat or is flowing through delivery pipework, mixers, pumps and baffles continues to agitate and/or shear the composition, hereby preserving an even distribution of solid particles throughout the liquid carrier, but the container does not contain means to agitate or shear whilst the composition cools until it has solidified or at least cooled sufficiently for the carrier to become so viscous as to retard particle settling. The difference in temperature between the filling temperature and the quiescent solidification temperature can be large, often at least 15° C. and even being in the region of 20 to 30° C.

The instant invention selects particularly an arylene/alkylene block copolymer as segregation inhibitor. The block copolymer contains two opposite and apparently incompatible segments, such as in particular one hard relatively oil insoluble and one soft relatively oil soluble segment. This can be provided by incorporating into the copolymer both an aryl polymer block (A) to provide the hard/insoluble segment and a polyalkylene block segment (B) to provide a soft/soluble segment. Each block commonly comprises at least 50 or at least 100 monomeric units. Such copolymers tend to provide a three-dimensional network which extends through out the carrier liquid, through physical cross-links, possibly with the formation of relatively insoluble sub-microscopic particles of the particular block, otherwise called domains. The copolymers can be linear.

The aryl monomer polymerised to form one segment (A) commonly comprises styrene, though alternative monomers comprising two or more fused rings can be used too. The polyalkylene segment (B) can be derived from butadiene, isoprene, ethylene/butylene and ethylene/propylene. Di-block copolymers have the form A-B and triblock copolymers preferably have the form A-B-A. The di-block and tri-block copolymers can be employed separately or a mixture of both can be used. In the present invention, the settling inhibitor is very conveniently a triblock copolymer of polystyrene:polyethylene/butylene:polystyrene (SEBS) or polystyrene:polyethylene/propylene:polystyrene (SEPS), optionally in mixture with a related diblock, viz SEB or SEP, as the case may be. The weight proportion of polystyrene in the block copolymer is commonly in the region of 13 to 32%, and is very desirably from 27 to 31% by weight. In SEBS copolymers, desirably, the weight proportion of the two polystyrene blocks is similar or equal. Where a mixture of triblock and diblock copolymers are employed, the weight ratio is conveniently in the range of from 75:25 to 25:75. It is very suitable to employ block copolymers that are of intermediate molecular weight, such as for example that of Kraton G-1650™, ±25%.

The segregation inhibitor, and particularly the block copolymer can be introduced into the composition in the form of a solid, especially when it is desired to form a translucent composition or as a gel in a hydrophobic water-immiscible liquid.

The segregation inhibitor, and particularly the block copolymer, is desirably incorporated into the composition in an amount of from at least 3% and particularly at least 4%, and normally not greater than 12%, percentages being by weight of the composition. In a number of desirable compositions, its weight proportion is often in the range of from 7 to 10%. The segregation inhibitor is suitably employed a weight ratio to the fibre-forming amide gellant of from 1:1 to 4:1, preferably at least 1.25:1, and especially at least 2:1. In many convenient embodiments, the weight ratio of segregation inhibitor to amide gellant is up to 3:1, for example from 1.25:1 to 3:1. When the amide gellant is gellant (1), by itself or together with gellant (2), an attractive balance of effectiveness against cost can be achieved at a weight ratio of segregation inhibitor to amide gellant of from 1.4 to 2:1.

It can also be convenient to relate the settling agent to the carrier liquid, and beneficially, the agent is incorporated at a weight ratio to the carrier liquid in the range of from 1:5 to 1:12, and particularly from 1:5 to 1:8.

Desirably, the weight of block copolymer plus N-acyl aminoacid amide is selected in the range of from 5 to 20% of the composition, preferably from 10 to 16%. In a number of chosen embodiments, the weight ratio of block copolymer plus N-acyl aminoacid amide to carrier fluid is selected in the range of from 1:4 to 1:6.

Carrier Fluid

In compositions herein, the carrier liquid comprises a non-volatile silicone oil and/or an aromatic ester oil. It is especially desirable that at least 50% and particularly at least 75% of the carrier liquid is the non-volatile silicone oil or aromatic ester oil having a refractive index of at least 1.50, and advantageously an aromatic ester oil. It is desirable for such non-volatile silicone oil and/or aromatic ester oil and their proportion thereof in the carrier liquid to have a refractive index sufficiently high to enable the entire carrier fluid, which may include a proportion of other water-immiscible oils of lower RI, to attain an RI of least 1.50 preferably at least 1.51, especially in some embodiments of at least 1.52 and very desirably at least 1.53. The mixture of carrier oils is in practice selected in the light of the refractive index of the antiperspirant active. The higher refractive index carrier oil mixtures are particularly suitable for employment with aluminium-zirconium chlorohydrates (and complexes thereof).

In practice preferred silicone or ester oils have an RI of not higher than 1.57. The choice of oils with a comparatively high RI such as at least 1.52 and particularly at least 1.53 renders it easier to obtain translucent formulations for a various types of antiperspirant actives.

The term aromatic ester oil relates to an ester which contains at least one aromatic group, preferably a benzoate or substituted benzoate group or naphthenoate, and which is liquid in the range of from 20 to at least 100° C. and preferably up to 150° C. Within the term aromatic ester oils, most oils satisfy the general formula $R^1$—$CO_2$—$R^E$ in which $R^1$ represents a phenyl group and $R^E$ represents an aryl or alkaryl group, the latter optionally containing an ether or ester linkage interposed between the alkenyl and aryl moieties within the group. The composition can also comprise benzyl benzoate, though alternative aryl esters as indicated below are much preferred on account of their superior sensory properties.

A subclass of particularly preferred aromatic esters satisfies the general formula

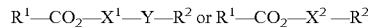
$R^1$—$CO_2$—$X^1$—Y—$R^2$ or $R^1$—$CO_2$—$X^2$—$R^2$ in which $R^1$ represents phenyl (as previously) $R^2$ also represents a phenyl group, $X^1$ represents an alkylene group containing from 2 to 4 carbons including at least one pendant alkyl group and Y represents a bond, or an ether or ester linkage and $X^2$ represents a linear alkylene group containing from 2 to 4 carbons.

Oils in this subclass are particular suitable for formulating translucent compositions on account of their comparatively high refractive index, typically being within the range of from 1.52 or 1.53 to 1.57.

Herein, it is particularly preferred to employ an alkylene group $X^1$ having a pendant alkyl group such as methyl or ethyl so as to improve other physical properties of the ester oil, such as appearance or sensory properties. Especially desirably, the alkylene group $x^1$ is isopropylene viz —CH(Me)—$CH_2$—.

When Y represents a bond, the alkylene group is bonded directly to aryl group $R^2$. Preferably Y represents an ester or ether linkage. In a number of highly desired embodiments X and Y together represent —CH(Me)—$CH_2$—O— or —CH(Me)—$CH_2$—$O_2$C— and especially —CH(Me)—$CH_2$—O—.

$X^2$ is a linear polymethylene group, preferably dimethylene. One especially desirable ester oil to employ comprises 2-phenylethyl benzoate.

The carrier liquid employed herein can conveniently comprise a non-volatile silicone oil (non-volatile siloxane), such as for example a linear di or triphenylmethylsiloxane containing preferably 1 to 1.5 phenyl groups per silicon atom. Alternatively, the non-volatile silicone oil can be an aryl substituted siloxane which satisfies the general formula

$R^J R^A{}_2 Si$—O—[—$SiR^K R^A$—O]$_n$—$SiR^L R^A{}_2$ in which n represents an average number of from 0 to 2

$R^J R^K$ and $R^L$, which may be the same as or different from each other, each represents a group $R^M$ of formula

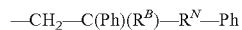
—$CH_2$—C(Ph)($R^B$)—$R^N$—Ph in which $R^B$ represents H or —$CH_3$ and $R^5$ represents an alkylene group containing from 0 to 3 carbon atoms, optionally branched and not more than one of $R^J$ $R^K$ and $R^L$ can optionally represent $R^C$, namely the hydrogenated residue of a substituted vinyl group other than $R^M$ or a residue of an aliphatic alcohol, a cycloaliphatic alcohol or an aralkyl alcohol and $R_A$ represents a $C_1$ to $C_4$ alkyl group provided that at least 60% of carbon atoms in total in substituents $R_A$ $R^M$ and $R^C$ are present in aryl groups. Such silicone oils can be obtained by catalytically reacting a corresponding starting material in which $R^K$ represents hydrogen with an olefin bearing the aromatic substitution.

In a preferred examples of such silicone oils $R^M$ represents a diphenylethyl group and such oil is obtainable by reacting the corresponding starting material with diphenylethylene.

Other suitable non-volatile silicone oils comprise di or tri methylphenylsiloxanes, such as methylphenyltrisiloxane (commercially available as DC704™ from Dow Corning Inc.)

The weight proportion of carrier liquid in the composition is often selected in the range of at least 40%, in many desirable formulations is up to 80%, a convenient range is from 40 to 70%.

In addition to the aforementioned oils having a high refractive index, the residue of the liquid carrier can comprise one or more supplementary oils. Such oils are likewise water-immiscible and a melting point of below 20° C. are miscible with the silicone and ester oils of high refractive index, but have a refractive index below 1.50 (at 25° C.)

One especially desirable class of supplementary oils comprises water-immiscible aliphatic alcohols which are liquid at 20° C. and have a boiling point of higher than 100° C. These include branched chain alcohols of at least 10 carbon atoms and in many instances up to 30 carbon atoms, particularly 15 to 25, such as isostearyl alcohol, hexyl-decanol and octyl-dodecanol. Other suitable water-immiscible alcohols include intermediate chain length linear alcohols, commonly containing from 9 to 13 carbon atoms, such as decanol or dodecanol. A further suitable alcohol is benzyl alcohol. Such alcohols can assist in the process of forming a solution of the amide-gellants in a water-immiscible carrier liquid during the manufacture of structured gels.

Such alcohols can often constitute from at least 5% by weight of the composition, commonly not greater than 15-20% and in many embodiments, from 7.5 to 12.5%. When expressed in terms of the carrier liquid fraction of the composition, such alcohols preferably constitute from 10% or 15% by weight of the water-immiscible liquid carrier mixture, and in many desirable mixtures comprising up to 25% or 30% of the carrier mixture. In a number of highly desirable formulations, the proportion of such aliphatic alcohols in said mixture is from 15% to 22% by weight.

However, aliphatic alcohols which are solid at 20° C., normally linear alcohols, such as stearyl alcohol are preferably absent or present in no more than 3% (particularly no more than 1%) by weight of the whole composition, as indicated hereinbefore, since they lead to opaque formulations and visible white deposits when a composition is topically applied to skin.

It is preferable for the carrier liquid to contain no more than 10% by weight (based on the carrier liquid mixture) of supplementary carrier fluid other than the aforementioned class of alcohol oils, especially not more than 5%, and if desired such other supplementary fluids can be absent. Other supplementary carrier oils can comprise water-immiscible ester oils having a refractive index of below 1.50, such as alkyl benzoates such as $C_{12-15}$ alkyl benzoates, including commercially available oils from Finetex under their mark Finsolv, eg Finsolv TN™. A further class of supplementary water-insoluble carrier oils comprises water-immiscible polyalkoxylated ethers, such as the CTFA listed PPG-14 butyl ether (commercially available as Fluid AP™) and related ethers. Although a small fraction of a volatile silicone oil can be tolerated, it is desirably no greater than 5 or 10% by weight of the carrier oils. Such volatile oils include cyclomethicones or dimethicone oils containing 4, 5 or 6 silicone atoms and volatile indicates a measurable vapour pressure of greater than 1 and preferably greater than 10 Pa at 25° C. Such volatile silicones are commercially available from Dow Corning Inc as DC245 or DC3345. Yet other water-immiscible supplementary oils comprise hydrocarbon including mineral oils and hydrogenated polydecene.

It will recognised that the proportion of any supplementary oil selected in conjunction with the proportion of ester oil and/or non-volatile silicone oil having an RI of at least 1.50 and preferably at least 1.57 to achieve acceptable refractive index matching with the suspended antiperspirant active particles, and preferably within 0.001 to 0.005 units.

Antiperspirant Actives

Antiperspirant actives are incorporated in the present composition in an amount of from 1-35%, and particularly from 5 or 10% to 30% of the weight of the composition. It is often considered that the main benefit from incorporating of up to 5% of an antiperspirant active in a stick composition is manifest in reducing body odour, and that as the proportion of antiperspirant active increases, so the efficacy of that composition at controlling perspiration increases.

Antiperspirant actives for use herein are selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference and comprise an enhanced Band 3 proportion of polymeric species of at least 20%. Such activated aluminium chlorohydrates can be made by a method in which the weight concentration of aluminium compounds in the solution is controlled within specified limits (desirably below and particularly well below 30-40%) and simultaneously the temperature of that solution is controlled within a specified elevated temperature range whilst polymeric aluminium species are formed, and drying conditions are strictly controlled as described in the said EP-A-6739. Various commercially available antiperspirant actives are stated by their manufacturers to be activated or offer enhanced activity and they can be considered to satisfy the term "activated" when employed herein.

Zirconium actives can usually be represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine, or an activated variant thereof. Actives of this preferred type (including activated variant (AZAG) are available from B G Giulini, Reheis, Summit and Westwood, though with differing particle size distributions. Consequently, such actives would become suitable for employment in the instant invention if their-production has been suitably adapted to meet the invention particle size criteria, or the product sieved or otherwise separated to attain a desired particle distribution.

The proportion of solid antiperspirant salt in a suspension composition normally includes the weight of any water of hydration and any complexing agent that may also be present in the solid active.

The particulate antiperspirant employed in the instant invention normally has a refractive index (RI) of at least 1.49 and not higher than 1.57. Actives which are activated tend to have a refractive index of at least 1.50. Actives which are free from zirconium tend to have an RI of from 1.49 to 1.54, depending on their formula and at least partly on their residual water content. Likewise, actives which contain zirconium tend to have an RI of from 1.52 to 1.57. The water content of the antiperspirant active can be modified by hydration after dried active has been made or by drying to an intermediate water content, the refractive index tending to vary inversely with water content. The actives can also be treated with a small amount of an alcohol such a $C_2$ to $C_4$ aliphatic alcohol, eg ethanol, to alter its RI.

Herein, the RIs of the antiperspirant active and the suspended antiperspirant active are matched to within 0.01. Herein, RIs and differences between them are those at 22° C. unless otherwise specified. Preferably, the difference between the refractive indices is less than 0.005. This can be achieved by varying the proportions of liquids constituting the carrier, its resultant RI being a weight averaged RIs of the carrier constituents and/or by varying the RI of the antiperspirant active as indicated above. Under many circumstances, RI matching of the constituents of the invention formulations is not absolutely perfect. Small variations can arise in practice, for example from changes in temperature or between different batches of ingredients. Thus, such RI difference in the invention compositions herein on the shelf or in the home is often at least 0.0005, and sometimes at least 0.001. Advantageously, by selecting the particulate antiperspirant active in accordance with the criteria described herein, and particularly with increasingly preferred criteria, the benefit of clear formulations can be retained even when the above-mentioned RIs do not match exactly.

The antiperspirant active employed herein comprises small particles, of which preferably not more than 60% by weight, desirably not more than 50% by weight have a diameter of below 10 μm. Preferably less than 40% and more preferably between 40 and 25% of particles by weight have a particle size of below 10 μm. In practice, desirable antiperspirant actives contain at least 1% and often at least 5% by weight of their particles in the range of from 1 to below 10 μM. In general, at least 90% by weight of the antiperspirant active has a particle size of below 100 μm, in many instances at least 95% by weight and in some preferred compositions at least 99% by weight below 100 μM. In many embodiments herein, the active has a weight average particle size of from 9 to 50 μm and particularly at least 10 μm, such as from 12 to 40 μm. It is desirable to select the weight average of the antiperspirant active in conjunction with the or preferred constraints on the proportion of particles of below 10 μm diameter as indicated above. It will be recognised that materials simply having such an average particle size are less suitable than those that also meet the respective criterion given above about maximum weight proportion of particles below 10 μm, in order to optimise product clarity, but of course an improvement in antiperspirant segregation is attained. A further increase in product clarity is attainable by employing an active in which up to 25% by weight of the particles have a particle diameter of below 10 μm, but decreasing the proportion of such very small particles increases segregation difficulties. It can be highly desirable to balance the two effects by employing an active containing between 25 and 40% by weight of particles below 10 μm.

The fineness, coarseness and particle size distribution of antiperspirant actives that are produced can vary substantially, depending on their manner and conditions of manufacture, including the type of drying stage employed, and any subsequent processing stages, such as milling, and/or classification. Actives having an appropriate particle size distribution to satisfy the above selection criterion can be made by suitably controlling conventional drying and milling techniques in manners known to persons skilled in the art of making antiperspirant actives, so as to reduce the proportion of particles produced of sub 10 μm diameter. Methods can include control of droplet size in spray drying. Where a product is produced, for example by spray drying or freeze drying that has excessive proportion of sub 10 μm diameter particles, the proportion can be lowered by conventional classification apparatus.

Furthermore, it is highly desirable to employ antiperspirant active material which is free or substantially free from hollow particles. In this context, substantially free indicates a content of less than 10% by weight hollow spheres, and preferably less than 5% by weight. Some drying techniques, eg spray drying, can produce materials which contain greater than such a proportion of hollow spheres. The proportion of hollow spheres in such an antiperspirant material can be reduced by milling the particulate material, such as by ball or swing milling. Products with no more than a few hollow particles are considered to have no significant affect on the RI of the product—i.e. any effect is de minimis.

Optional Ingredients

Optional ingredients include wash-off agents, often present in an amount of up to 10% w/w to assist in the removal of the formulation from skin or clothing. Such wash-off agents are typically non-ionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more non-particulate cosmetic adjuncts conventionally contemplatable for cosmetic solids. Such cosmetic adjuncts can include deodorant actives, such as in an amount of up to 2%, skin benefit agents such as allantoin or lipids, for example in an amount of up to 5%; colours; skin cooling agents, such menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

A further class of optional ingredients can comprise particulate suspending aids or fillers, though normally in an amount of not more than 5% by weight. Such aids or fillers, which can include silicates, clays or talc, are selected to have a refractive index which is similarly matched to that of the carrier fluid mixture, so that the maximum RI difference between particulate or carrier constituents of the composition is within the range or preferred range of RI difference between the RIs mentioned hereinbefore.

Benefits

The instant invention enables the manufacturer to obtain anhydrous suspension antiperspirant sticks having a reduced antiperspirant segregation between top and bottom of the stick whilst employing a gellant, such as a fibre-forming amide gellant, that has a higher solidification temperature under conditions of shearing of the fluid composition containing the dissolved gellant and suspended antiperspirant active that occur in processing vats and than its quiescent solidification temperature. This applies particularly in respect of compositions having a carrier liquid formulated so as to match the refractive index of carrier liquid and suspended antiperspirant active within 0.001, for example employing the carrier fluids and antiperspirant actives described herein. This benefit of reduced segregation applies particularly in respect of antiperspirant actives having a weight average particle size of at least 9 or 10 μm, for example up to 80 μm and particularly up to 50 μm, such as in the range of from 10 to 50 μm, conveniently from 12 to 35 μm. It is beneficial if such antiperspirant actives also have no more than a limited proportion of particles below 10 μm in diameter, such as less than 50% by weight.

Composition Preparation

The invention compositions can be prepared by a process according to claim 44 herein. It can be convenient to measure the RI of a sample of the batch of antiperspirant active to be used before carrying out the preparation, because there can be some variation between batches.

It is particularly desirable to delay the introduction of the antiperspirant active until after the gellant and segregation inhibitor have been dissolved, and especially until the resultant composition has cooled to a temperature intermediate between that at which the amide gellant is dissolved and the shearing solidification temperature of the complete composition. Where the composition is very similar to a previous composition, then the shearing solidification temperature of the latter can be taken as an approximation. Desirably, the antiperspirant active is introduced to form a composition that is from 5 to 15° C. often 5 to 10° C. above the shearing solidification temperature. By delaying the temperature at which the antiperspirant active is incorporated into the carrier liquid, water loss from the active-can be reduced or eliminated.

It is desirable to introduce the composition into the dispensing container or mould at a temperature of from 3 to 10° C. above the shearing solidification temperature of the composition.

Product Form

The sticks produced according to the present invention herein are clear, the extent of light transmission depending at least partly on the extent to which the refractive indices (RI) of the ingredients are matched and the particle size of the particulate antiperspirant is controlled. Clear formulations are possible in respect of the invention formulations because the selected structurant forms a fibrous structure within the liquid hydrophobic carrier that is not seen by the human eye and the RIs of the carrier liquid and the suspended antiperspirant active have been appropriate matched.

It is highly desirable to employ RI matching as indicated above, to enable the resultant composition to transmit at least 1% light (measured in accordance with test iv, Clarity of formulation—light transmission test described in U.S. Pat. No. 6,652,843 col 20) and especially at least 5% transmission.

Mechanical Properties and Product Packages

The compositions of this invention are structured liquids and are firm in appearance. A composition of this invention will usually be marketed as a product comprising a container with a quantity of the composition therein, where the container has an aperture for the delivery of composition, and means for urging the composition in the container towards the delivery aperture. Conventional containers take the form of a barrel of oval cross section with the delivery aperture at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is often closed.

Generally the container will include a cap for its open end and a component part which is sometimes referred to as an elevator platform or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a hand-wheel mounted on the barrel at its closed end, i.e. the opposite end to the delivery opening.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

In a further invention, there is provided an anhydrous antiperspirant or deodorant composition (an EPB composition) which comprises:

a) from 1 to 35% by weight of an antiperspirant active comprising a particulate astringent aluminium and/or zirconium salt having a refractive index of from 1.49 to 1.57 at 22° C, preferably of which less than 60% by weight of its particles have a diameter of up to 10 μm;

b) from 30 to 90% by weight of a water-immiscible carrier fluid in which said antiperspirant active is suspended comprising 2-ethylphenyl benzoate and;

c) a fibre-forming amide gellant for said carrier fluid.

In EPB compositions, the amide gellant can be selected in accordance with the foregoing description for compositions additionally containing the aforementioned segregation inhibitor. Likewise, the liquid carrier can optionally comprise one or more of the aforementioned non-volatile silicone oils and other ester oils of refractive index of at least 1.50 and/or supplementary carrier oils to form a carrier liquid in accordance with its description given for segregation inhibitor-containing compositions. Likewise the EPB compositions can contain one or more optional ingredients as described hereinabove for segregation inhibitor-containing compositions. The EPB formulations can be produced by a process described above, excluding the segregation inhibitor.

EXAMPLES

Having given a detailed description of the present invention, specific embodiments will now be described more fully by way of example only. The skilled man is able to modify those examples to create related compositions based on his common general knowledge which incorporate alternative or additional constituents in accordance the foregoing Detailed Description.

In these Examples, the ingredients employed were as follows:

Carrier Oils

Oil 1: 2-phenyl ethyl benzoate (Finsolv SUN ex Finetex)

Oil 2 2-propanol, 1-phenoxy benzoate (sample oil ex Degussa)

Oil 3 methyl phenyl trisiloxane (DC704 ex Dow Corning)

Supplementary Carrier Oil

Oil 4 Isostearyl alcohol (Prisorine 3515 ex Uniqema)

Gellants

Gel 1 GP-1: N-lauroyl-L-glutamic acid di-n-butylamide (Ajinomoto)

Gel 2 GA-01: N-(2-ethyl hexanoyl)-L-glutamic acid di-n-butylamide (Ajinomoto)

Gel 3 Aspartame based cyclo dipeptide—thymol derivative (made according to example 1.2 in WO03/059307

Gel 4 cis/trans-1,2-di(2-ethylhexan amido) cyclohexane (made according to example 1 of U.S. Pat. No. 6,410,003).

Segregation Inhibitor

SI 1 Styrene-ethylene/butylene-styrene Block Copolymer (Kraton G1650E ex Kraton Polymers)

SI 2 Styrene-butadiene block Copolymer (Kraton D1102 ex Kraton Polymers)

Antiperspirant Active

AP 1: Activated Al/Zr pentachlorohydrex glycine complex, RI 1.531, D50 13.1 μm, 39%<10 μm, few [de minimis] hollow particles (AP5G-LR (Sample A) ex B K Giulini)

AP 2: Activated Al/Zr pentachlorohydrex glycine complex, RI 1.531, D50 31.9 μm, 12.5%<10 μm, few [de minimis] hollow particles (AP5G-LR (Sample B) ex B K Giulini)

AP 3 AACH: Activated aluminium chlorohydrate, RI 1.530, D50 17.4 μm, 25.4%<10 μm, few [de minimis] hollow particles (A418™ ex Summit)

The example and comparison compositions were made by the following method, except as indicated hereinafter. In preliminary steps, the refractive index of the carrier liquid and antiperspirant active as either measured using a conventional apparatus/method at 22° C. or calculated from data provided on the product data sheet for commercial liquid products, and the respective proportions of the constituents of the carrier liquid calculated (weight averaged RIs of individual constituents) in order to attain RI matching within 0.0006 units.

Stage 1—a dispersion of the segregation inhibitor (block copolymer) in the ester oil and/or non-volatile silicone oil at 15% w/w was obtained by heating a mixture of the two constituents to 120-125° C. and stirring the mixture at that temperature until the solid was seen by eye to have fully dispersed in the liquid, and then allowing the dispersion to cool overnight to laboratory ambient temperature (circa 22° C.);

Stage 2—the particulate antiperspirant active was introduced with gentle stirring into the mixture of stage 1 and de-aerated under vacuum;

Stage 3—the gellant or gellant mixture was dissolved in the supplementary carrier oil by heating to circa 120° C. and stirring, and the solution allowed to cool to 110-105° C.;

Stage 4—the mixture of stage 2 was heated ca. 80-85° C. by oil bath with relatively gentle stirring to avoid re-introduction of air;

Stage 5—the solution of stage 3 was added to the mixture of stage 4 and mixed well for 2 minutes at a temperature of circa 85-87° C.;

Stage 6—Under constant stirring, fragrance was introduced into the mixture of stage 5 and cooled to circa 75° C. Tests indicated that the solidification temperature of the compositions was approximately 70° C. under the prevailing shearing conditions.

Stage 7—the complete formulation (circa 45 g) was poured at circa 75° C. into an inverted conventional dispensing container to a depth of about 6 cm from a concave domed former to an elevator (piston)—a conventional so-called bottom fill process. The spindle and thumb-wheel were than inserted.

Stage 8—the filled container was allowed to cool to laboratory ambient temperature whilst remaining in an invert orientation.

Stage 9—the clarity of the compositions was assessed and samples of the composition were taken and analysed for antiperspirant active content by the method indicated below.

Tests indicated that the solidification temperature of the compositions was approximately 550C under quiescent conditions.

In Comparisons D and F and Examples 7 and 9, the Segregation Inhibitor was dissolved in the oils in stage 2. The pour temperature (stage 7) for CompF and Ex9 was 79° C. rather than 75° C., because the shearing solidification temperature was about 74/75° C.

When the sticks had cooled to ambient, their light transmittance was estimated by the eye of an experienced cosmetic chemist. All the comparisons and examples were judged to be clear/translucent.

In stage 9, the distribution of antiperspirant active within the stick from top to bottom was determined by measuring the antiperspirant active content in samples of the stick composition extracted respectively from the dome (created by the former) within 5 mm of its apex or within 5 mm of its point of contact with the elevator/piston (bottom). The samples were approximately 5-5.5 cm apart. The antiperspirant active content of each sample was measured using the Metrohm 716 DMS Titrino Chloride Analysis Rig with Auto-titrator.

A weighed sample of 0.5 g was removed from respectively the dome or bottom of a stick and deposited into a 250 ml beaker. Ethanol (40 mls) was then introduced and the beaker swirled to break up the sample. Nitric acid (10 mls) was then introduced into the beaker which was swirled once again. The resultant mixture was then heated on a hotplate in a fume cupboard to 60° C. for 10 minutes to dissolve the antiperspirant active. The beaker was removed from the hotplate and distilled water was added up to the 200 ml mark. The weight of the sample was then entered into the machine before the electrode and paddle/auto-titrator facility were lowered into the beaker. An autotitration was carried out by the machine which calculated and displayed (in a print-out) the proportion of chloride in the sample.

The chloride content of each antiperspirant active had already been determined by the same method using the same apparatus. By comparing the proportion of chloride in the antiperspirant active employed in the composition with that measured in the respective samples extracted from the stick, the proportion of antiperspirant active in each sample was calculated. The difference between the weight proportions of antiperspirant in the dome (top) and at the bottom of the dispensing container is summarised in the Tables below as the "Span". The larger the Span, the worse is the segregation in the stick.

TABLE 1

| Ingredients | CompA | Ex1 | Ex2 | Ex3 | CompB | CompC | Ex4 | Ex5 | Ex6 |
|---|---|---|---|---|---|---|---|---|---|
| | | | | | % by weight | | | | |
| Gel 1 | 2.5 | 2.5 | 2.5 | 2.5 | 2.5 | 2.5 | 2.5 | 2.5 | 2.5 |
| Gel 2 | 2.5 | 2.5 | 2.5 | 2.5 | 2.5 | 2.5 | 2.5 | 2.5 | 2.5 |
| Oil 1 | 59.06 | 53.15 | 51.68 | 50.21 | 59.06 | 54.63 | 53.15 | 51.68 | 50.21 |
| Oil 4 | 11.44 | 11.44 | 11.44 | 11.44 | 11.44 | 11.44 | 11.44 | 11.44 | 11.44 |
| SI 1 | | 5.91 | 7.38 | 8.85 | | 4.43 | 5.91 | 7.38 | 8.85 |
| AP 1 | 23.5 | 23.5 | 23.5 | 23.5 | | | | | |
| AP 2 | | | | | 23.5 | 23.5 | 23.5 | 23.5 | 23.5 |
| Fragrance | 1.0 | 1.0 | 1.0 | 1.0 | 1.0 | 1.0 | 1.0 | 1.0 | 1.0 |
| Characteristics | | | | | | | | | |
| Dome % AP | 27.41 | 24.83 | 25.40 | 23.96 | 54.94 | 42.93 | 28.62 | 28.45 | 28.68 |
| Bottom % AP | 24.25 | 23.16 | 23.45 | 23.27 | 14.20 | 11.26 | 17.99 | 15.80 | 21.03 |
| Span | 3.16 | 1.67 | 1.96 | 0.69 | 40.75 | 31.67 | 10.63 | 12.64 | 7.64 |

TABLE 2

| Ingredients | CompD | Ex7 | CompE | Ex8 | CompF | Ex9 |
|---|---|---|---|---|---|---|
| | | | % by weight | | | |
| Gel 1 | 2.5 | 2.5 | 2.5 | 2.5 | 2.5 | 2.5 |
| Gel 2 | 2.5 | 2.5 | 2.5 | 2.5 | 2.5 | 2.5 |
| Oil 1 | | | 59.06 | 50.21 | 40.93 | 34.789 |
| Oil 2 | | | | | 19.56 | 16.63 |
| Oil 3 | 56.44 | 50.80 | | | | |
| SI 1 | | 5.64 | | 8.85 | | 9.08 |
| Oil 4 | 14.05 | 14.05 | 11.44 | 11.44 | 10.01 | 10.01 |
| AP 2 | 23.5 | 23.5 | | | 23.5 | 23.5 |
| AP 3 | | | 23.5 | 23.5 | | |
| Fragrance | 1.01 | 1.01 | 1.0 | 1.0 | 1.0 | 1.0 |
| Characteristics | | | | | | |
| Dome % AP | 43.85 | 29.14 | 29.99 | 24.31 | 44.08 | 24.02 |
| Bottom % AP | 10.63 | 23.28 | 20.11 | 23.22 | 8.85 | 23.16 |
| Span | 33.22 | 5.86 | 9.88 | 1.09 | 35.23 | 0.86 |

TABLE 3

| Ingredients | CompG | Ex10 | CompH | Ex11 | CompB | Ex12 |
|---|---|---|---|---|---|---|
| | | | % by weight | | | |
| Gel 1 | 4 | 4 | 2 | 2 | 2.5 | 2.5 |
| Gel 2 | | | 2 | 2 | 2.5 | 2.5 |
| Gel 3 | 1 | 1 | | | | |
| Gel 4 | | | 1 | 1 | | |
| Oil 1 | 59.06 | 50.51 | 59.06 | 50.21 | 59.06 | 53.15 |
| Oil 4 | 11.44 | 11.44 | 11.44 | 11.44 | 11.44 | 11.44 |
| SI 1 | | 8.85 | | 8.85 | | |
| SI 2 | | | | | | 5.91 |
| AP 2 | 23.5 | 23.5 | 23.5 | 23.5 | 23.5 | 23.5 |
| Fragrance | 1.0 | 1.0 | 1.0 | 1.0 | 1.0 | 1.0 |
| Characteristics | | | | | | |
| Dome % AP | 58.33 | 33.56 | 54.77 | 28.39 | 54.94 | 24.60 |
| Bottom % AP | 4.2 | 20.17 | 5.86 | 20.11 | 14.20 | 22.70 |
| Span | 54.13 | 13.39 | 48.91 | 8.28 | 40.75 | 1.90 |

From Tables 1 to 3, by comparing the Example formulation with the corresponding Comparison formulation or formulations, it can be seen that the addition of the segregation inhibitor substantially reduced the extent of segregation. Thus, a comparison of CompA with the Examples 1 to 3 showed a significantly reduced Span for the Examples, even though the Span in the Comparison was 3.16% (because the average particle size of the antiperspirant active (AP1) tended to be rather small. When an antiperspirant active having a larger average particle size was employed, AP2, the Tables show that the extent of segregation was substantially greater, for example by comparing Comparisons A and B. However, by comparing CompB and CompC with Examples 4 to 6, it is evident that a substantial reduction of segregation has been achieved. In addition, by comparing CompC with Example 4, it can be seen that a significant increase in the effectiveness of the segregation inhibitor occurred when the ratio of segregation inhibitor to gellant was increased from about 0.88:1 to 1.18:1.

Tables 1 and 2 show that it is especially beneficial to employ a mixture of gellants (1a) and (1b) as the gellant for the composition.

The Tables also show that it is particularly beneficial to employ an ester oil having a high refractive index as described herein as the principal carrier liquid.

The invention claimed is:

1. An anhydrous antiperspirant or deodorant composition comprising:
   a) from 1 to 35% by weight of an antiperspirant active comprising a particulate astringent aluminium and/or zirconium salt having a refractive index of from 1.49 to 1.57 at 22° C. of which less than 60% by weight of its particles have a diameter of up to 10 μm;
   b) from 30 to 90% by weight of a water-immiscible carrier fluid in which said antiperspirant active is suspended having a refractive index of at least 1.50 at 22° C. that is matched within 0.01 refractive index units of the antiperspirant active and comprising a non-volatile silicone oil and/or an aromatic ester oil;
   c) at least one fibre-forming amide gellant for said carrier fluid selected from the group consisting of acyl aminoacid amides, cyclic dipeptides, 1,2-bisamidocyclohexanes, 1,3-bisamidocyclohexanes, amide derivatives of 1,2-dicarboxylic acids, amide derivatives of 1,3-dicarboxylic acids, and amide derivatives of 1,2,3-tricarboxylic acides, and
   d) a segregation inhibitor in a weight ratio to said fibre-forming amide gellant of from 1:1 to 3:1, wherein said segregation inhibitor is an alkylene-arylene block copolymer.

2. A composition according to claim 1 in which the carrier fluid comprises an oil or mixture of oils having a refractive index of up to 1.57.

3. A composition according to either claim 1 characterized in that at least 50% by weight of the carrier fluid is a non-volatile silicone oil or an aromatic ester oil having a refractive index of at least 1.52.

4. A composition according to claim 1 in which at least 75% by weight of a carrier fluid is an aromatic ester oil, and wherein up to 25% by weight of the antiperspirant active particles have a particle diameter of below 10 μm.

5. A composition according to claim 1 in which the aromatic ester oil satisfies the general formula:

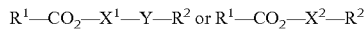

$R^1$—$CO_2$—$X^1$—Y—$R^2$ or $R^1$—$CO_2$—$X^2$—$R^2$ in which $R^1$ and $R^2$ each represent a phenyl group, $X^1$ represents an allkylene group containing from 2 to 4 carbons including at least one pendant alkyl group and Y represents a bond, or an ether or ester linkage and $X^2$ represents a linear alkylene group containing from 2 to 4 carbons.

6. A composition according to claim 5 in which $X^1$ or $X^2$ represents a dimethylene group.

7. A composition according to claim 5 in which $X^1$ represents —CH(Me)-$CH_2$—.

8. A composition according to claim 7 in which Y represents an ether or ester linkage.

9. A composition according to any claim 1 in which the non-volatile silicone oil comprises an aryl substituted siloxane which satisfied the general formula

$R^1R^4_2Si$—O—$[SiR^2R^4$—O$]_n$—$SiR^3R^4_2$ in which n represents an average number of from 0 to 2

$R^1$ $R^2$ and $R^3$, which may be the same as or different from each other, each represents a group $R^4$ of formula —$CH_2$—$C(Ph)(R^B)$—$R^5$-Ph in which $R^B$ represents H or —$CH_3$ and $R^5$ represents an alkylene group containing from 0 to 3 carbon atoms, optionally branched And not more than one of $R^1$ $R^2$ and $R^3$ can optionally represent $R^C$, namely the hydrogenated residue of a substituted vinyl group other than $R^4$ or a residue of an aliphatic alcohol, a cycloaliphatic alcohol or an aralkyl alcohol And $R^4$ represents a $C_1$ to $C_4$ alkyl group provided that at least 60% of carbon atoms in total in substituents $R^4$ $R^4$ and $R^C$ are present in aryl groups.

10. A composition according to claim 1 in which the non-volatile silicone oil comprises methylphenyltrisiloxane.

11. A composition according to claim 1 in which the amide gellant comprises an N-acyl aminoacid amide.

12. A composition according to claim 1 in which the N-acyl aminoacid amide comprises N-lauroyl-L-glutamic acid di-n-butylamide and/or N-(2-ethylhexanoyl)-L-glutamic acid di-n-butylamide.

13. A composition according to claim 1 in which the amide gellant comprises a cyclodipeptide.

14. A composition according to claim 1 in which the amide gellant comprises a 1,2 or 1,3 bisamido cyclohexane.

15. A composition according to claim 1 in which the amide gellant comprises an amido derivative of a di or tricarboxylic acid.

16. A composition according to claim 1 in which the proportion of fibre-forming amide gellant in the composition is selected in the range of from 0.6 to 10% by weight.

17. A composition according to claim 16 in which the composition contains at least 2% by weight of an N-acyl aminoacid amide.

18. A composition according to claim 1 in which the fibre-forming gellant is from 2 to 15% by weight of the carrier liquid.

19. A composition according to claim 18 in which the fibre-forming gellant is from 6 to 10% by weight of the carrier liquid.

20. A composition according to claim 1 in which the arylene alkylene block copolymer comprises a di or tri-block copolymer.

21. A composition according to claim 1 in which the arylene alkylene block copolymer comprises a styrene block copolymer.

22. A composition according to claim 21 in which the styrene block copolymer comprises a styrene-butylene, styrene-ethylene, or styrene-propylene block copolymer.

23. A composition according to claim 21 in which the styrene block copolymer comprises a styrene-ethylene/butylenes block copolymer.

24. A composition according to claim 21 in which the styrene block copolymer comprises a styrene-ethylene/butylenes-styrene triblock copolymer, optionally together with a styrene-ethylene/butylenes diblock copolymer.

25. A composition according to claim 21 in which the weight proportion of styrene in the copolymer is from 27 to 31%.

26. A composition according to claim 1 in which the segregation inhibitor is present in an amount selected in the range of from 3 to 12%.

27. A composition according to claim 1 wherein the weight of segregation inhibitor plus fibre-forming amide gellant is in the range of from 5 to 20% of the composition.

28. A composition according to claim 1 in which the weight ratio of segregation inhibitor plus amide gellant to carrier fluid is selected in the range of from 1:4 to 1:6.

29. A composition according to claim 1 in which the antiperspirant active comprises an aluminium and/or zirconium chlorohydrate or a complex thereof.

30. A composition according to claim 29 in which the antiperspirant active comprises an activated aluminium chlorohydrate.

31. A composition according to claim 29 in which the antiperspirant active comprises an aluminium zirconium chlorohydrate, optionally complexed with an amino acid.

32. A composition according to claim 31 in which the antiperspirant active comprises an aluminium zirconium chlorohydrate-glycine complex.

33. A composition according to claim 1 in which between 25% and 40% by weight of the antiperspirant active has a particle diameter of below 10 μm.

34. A composition according to claim 1 in which the antiperspirant active has a weight averaged mean particle size of from 9 to 50 μm.

35. A composition according to claim 1 in which the carrier fluid has a refractive index that is matched to within 0.005 units of the antiperspirant active.

36. A composition according to claim 35 in which the refractive index of the carrier fluid is matched to within 0.001 to 0.005 units of the antiperspirant active.

37. A composition according claim 1 in which the carrier fluid additionally comprises an aliphatic monohydric alcohol having a boiling point in excess of 100° C.

38. A composition according to claim 37 in which the aliphatic monohydric alcohol is iso-stearyl alcohol.

39. A composition according to claim 37 in which the aliphatic monohydric alcohol provides from 5 to 15% by weight of the composition.

40. A composition according to claim 37 in which the aliphatic monohydric alcohol provides from 15 to 20% by weight of the carrier fluid.

41. A process for preparing an antiperspirant composition as described in claim 1 which comprises the steps of
  dissolving a fibre-forming amide gellant and a segregation inhibitor in a carrier fluid having a refractive index of at least 1.50 at 22° C. that is matched within 0.01 refractive index units of the antiperspirant active and comprising a non-volatile silicone oil and/or an aromatic ester oil at an elevated temperature; mixing the carrier fluid with a particulate antiperspirant active either before or after or during dissolution of the fibre-forming amide gellant and a segregation inhibitor; cooling the composition containing the dissolved fibre-forming amide gellant and segregation inhibitor and whilst the composition is still mobile filling a dispensing container or mould.

42. A process according to claim 41 in which the antiperspirant active is mixed with the carrier fluid after dissolution of the fibre-forming amide gellant at a temperature intermediate between that at which the fibre-forming amide gellant dissolved and that at which the dispensing container or mould is filled.

43. A method of reducing sedimentation in a process for making a solid antiperspirant composition comprising the steps of dissolving at least one fibre-forming amide gellant selected from the group consisting of acyl aminoacid amides, cyclic dipeptides, 1,2-bisamidocyclohexanes, 1,3-bisamidocyclohexanes, amide derivatives of 1,2-dicarboxylic acids, amide derivatives of 1,3-dicarboxylic acids, and amide derivatives of 1,2,3-tricarboxylic acids in a carrier fluid having a refractive index of at least 1.50 at 22° C. and comprising a non-volatile silicone oil and/or an aromatic ester oil at an elevated temperature;
  mixing the carrier fluid with particles of antiperspirant active either before or after or during dissolution of the amide gellant;
  cooling the composition containing the dissolved amide gellant and whilst the composition is still mobile filling a dispensing container or mould in which a segregation inhibitor is dissolved in the carrier fluid before the composition is filled into the dispensing container or mould, wherein said segregation inhibitor is an arylene alkylene block copolymer and wherein the weight ratio of said segregation inhibitor to said fibre-forming amide gellant is from 1:1 to 3:1, and wherein up to 25% by weight of the antiperspirant active particles have a diameter of below 10 μm, and wherein the carrier fluid has a refractive index that is matched to within 0.01 refractive index units of the antiperspirant active.

44. An anhydrous antiperspirant or deodorant composition which comprises
  a) from 1 to 35% by weight of an antiperspirant active comprising a particulate astringent aluminium and/or zirconium salt having a refractive index of from 1.49 to 1.57 at 22° C., of which less than 60% by weight of its particles have a diameter of up to 10 μm;
  b) from 30 to 90% by weight of a water-immiscible carrier fluid in which said antiperspirant active is suspended comprising 2-ethylphenyl benzoate;
  c) a fibre-forming amide gellant for said carrier fluid; and
  d) from 3 to 12% by weight of an alkylene-arylene block copolymer,
  wherein the weight ratio of the alkylene-arylene block copolymer to the fibre-forming amide gellant is from 1:1 to 3:1.

45. A composition according to claim 44 wherein the carrier fluid further comprises a non-volatile silicone oil and/or an aromatic ester oil other than 2-ethylphenyl benzoate, which oil has a refractive index of at least 1.50 and is present in an amount less than the weight proportion of 2-ethylphenyl benzoate, and wherein up to 25% by weight of the antiperspirant active particles have a diameter of below 10 μm and wherein the antiperspirant active has a weight averaged mean particle size of from 12 to 35 μm.

46. A composition according to claim 1 wherein the weight of segregation inhibitor plus fibre-forming amide gellant is in the range of from 10 to 16% of the composition.

47. A composition according to claim 1 in which the antiperspirant active has a weight averaged mean particle size of from 12 to 35 μm.

* * * * *